United States Patent
Magel et al.

[11] Patent Number: 5,822,473
[45] Date of Patent: Oct. 13, 1998

[54] INTEGRATED MICROCHIP CHEMICAL SENSOR

[75] Inventors: Gregory Anton Magel, Dallas; Terrance Gus McDonald, Plano; Jau-Yuann Yang, Richardson; Han-Tzong Yuan, Dallas, all of Tex.

[73] Assignee: Texas Instruments Incorporated, Dallas, Tex.

[21] Appl. No.: 808,816

[22] Filed: Feb. 28, 1997

Related U.S. Application Data

[60] Provisional application No. 60/012,588 Feb. 29, 1996.

[51] Int. Cl.$^6$ .................................................. G02B 6/26
[52] U.S. Cl. .................................. 385/12; 385/14; 385/89
[58] Field of Search .................... 385/14, 88, 89, 385/92, 49, 129, 130, 131, 132, 12; 372/50

[56] References Cited

U.S. PATENT DOCUMENTS

| | | | |
|---|---|---|---|
| 4,824,206 | 4/1989 | Klainer et al. | 350/96.29 |
| 4,843,609 | 6/1989 | Ohya et al. | 372/50 |
| 4,846,548 | 7/1989 | Klainer | 350/96.29 |
| 4,892,383 | 1/1990 | Klainer et al. | 350/96.29 |
| 4,913,519 | 4/1990 | Klainer et al. | 350/96.29 |
| 4,929,049 | 5/1990 | LeGoullon et al. | 350/96.29 |
| 4,940,328 | 7/1990 | Hartman | 356/345 |
| 4,978,052 | 12/1990 | Fister et al. | 228/123 |
| 5,026,139 | 6/1991 | Klainer et al. | 350/96.29 |
| 5,105,255 | 4/1992 | Shannon et al. | 357/68 |
| 5,165,005 | 11/1992 | Klainer et al. | 385/129 |
| 5,235,140 | 8/1993 | Reele et al. | 174/267 |
| 5,237,130 | 8/1993 | Kulesza et al. | 174/260 |
| 5,261,014 | 11/1993 | Bruno et al. | 385/14 |
| 5,291,607 | 3/1994 | Ristic et al. | 395/750 |
| 5,315,672 | 5/1994 | Padovani | 385/12 |
| 5,346,857 | 9/1994 | Scharr et al. | 437/183 |
| 5,359,768 | 11/1994 | Haley | 29/840 |
| 5,370,301 | 12/1994 | Belcher et al. | 228/180.22 |
| 5,394,239 | 2/1995 | Valette | 356/345 |
| 5,405,583 | 4/1995 | Goswami et al. | 422/86 |
| 5,435,734 | 7/1995 | Chow | 439/69 |
| 5,438,477 | 8/1995 | Pasch | 361/689 |
| 5,452,118 | 9/1995 | Maruska | 385/14 |
| 5,555,127 | 9/1996 | Abelkader et al. | 385/14 |

*Primary Examiner*—John Ngo
*Attorney, Agent, or Firm*—Bret J. Petersen; James C. Kesterson; Richard L. Donaldson

[57] ABSTRACT

An optical device for sensing properties in an environment such as the presence of a substance or chemical in the zone to be monitored using optical components integrated on a microchip base or substrate. A preferred embodiment introduces a method for fabricating a miniature microchip chemical sensor by integrating a GaAs LED 14 with a polyimide waveguide 48 and a silicon photosensor 16 on the same chip. Light 18 is emitted at the edge of the GaAs LED 14. A portion of the light propagates is detected by a PIN diode 16. A chemical sensitive material 50 is coated on top of a polyimide waveguide 48. When the gas or chemical to which the material is sensitive appears, the light transmitted from the polyimide to air increases, thus the total signal sensed by the photodetector decreases, whereby the change in light signal indicates detection.

24 Claims, 1 Drawing Sheet

INTEGRATED MICROCHIP CHEMICAL SENSOR

CROSS-REFERENCES TO RELATED APPLICATIONS

The following concurrently filed application is related to the instant application and is incorporated herein by reference.

Ser. No. 08/808,373, TI-21382, "A FLIP-CHIP DIE ATTACHMENT FOR A HIGH TEMPERATURE DIE TO SEMICONDUCTOR SUBSTRATE BOND", filed Feb. 28, 1997, now U.S. Pat. No. 5,760,479.

FIELD OF THE INVENTION

This invention generally relates to optical devices and techniques for sensing properties of an environment, or the presence of a substance or chemical in the environment. More particularly, it relates to refractive index type chemical sensors using optical waveguides integrated on a microchip substrate. A preferred embodiment is described which uses a polyimide optical waveguide and a GaAs LED light source mounted on a circuit substrate such as a silicon IC chip containing a photosensor and signal conditioning circuitry to achieve a small, low-cost, high volume, integrated chemical sensor.

BACKGROUND OF THE INVENTION

Devices have been demonstrated that can detect the presence of chemical or a property of an environment by detecting a change in the index of refraction of an optical waveguide. Many of these sensors are based on optical fibers, which guide light through the core of a fiber by total internal reflection at the core/cladding interface using a cladding of lower refractive index than the core. Others are based on a waveguide core on a semiconductor substrate. In either case, these chemical sensors typically use the principle that some materials exhibit a change in index of refraction when exposed to a substance or change in the environment. Therefore, a change in the environment can be detected by monitoring changes in the light signal traveling in the waveguide caused by the change in the index of refraction of the cladding.

For example, U.S. Pat. No. 4,846,548 to Klainer, discloses a refractive index chemical sensor which uses a sensitive coating applied to a fiber optic core which can sense the presence of a chemical in an environment where the chemical reacts with the sensitive coating to produce a change in the coating's index of refraction.

U.S. Pat. No. 4,940,328, to Hartman, discloses a device that detects a property of the environment by injecting a light beam into a waveguide such that at least two modes of the beam propagate in the waveguide. An electrical signal is generated representative of the interfering product of the two modes of the beam that have propagated through the waveguide. The product is a function of the index of refraction which is affected by the property of the environment to be sensed.

Further, U.S. Pat. No. 5,165,005, to Klainer et al., discloses a refractive index chemical sensor which uses planar waveguides. This sensor uses a metal cladding segment on a planar waveguide that has an affinity for a species of chemical to be sensed to produce a controlled leakage of light from the waveguide through the metal clad segment when the species to be sensed comes in contact with the segment.

SUMMARY OF THE INVENTION

In accordance with the present invention, an integrated micro-chip chemical sensor and method of fabrication is provided for a device to sense the presence of a property in an environment. The present invention introduces a small, low-cost integrated device which overcomes the problems in the prior art. In addition to the large size of prior art devices, a particular problem was the costly and labor intensive problem of alignment of the light source, waveguide, and photodetector. The present invention can eliminate this problem by providing a structure which is essentially "self-aligned."

A further advantage of an embodiment of the present invention is a highly sensitive sensor without the need for calibration to reduce the affects of background noise. In this embodiment, enhanced sensitivity without calibration is made possible by a bridge circuit design which uses four detectors with a single source LED for common mode rejection of noise.

Another advantage of an embodiment of the present invention is simple integration of the sensor with other circuits such as a signal processor. Where an embodiment includes signal conditioning such as described for a preferred embodiment, the output of the sensor can be directly connected to other signal processing circuitry.

The present invention generally provides lower cost, higher reliability, and lower power consumption due to complete integration of the light source, waveguide, detector and possibly signal conditioning circuits on the same substrate for a high volume production device.

An embodiment of the present invention introduces a method for fabricating a miniature microchip chemical sensor by integrating a GaAs LED with a polyimide waveguide with a silicon photosensor on the same chip. The light is emitted at the edge of the GaAs LED. Part of the light propagates toward the polyimide/photodetector interface, while part of the light propagates toward the air/polyimide interface. At the air/polyimide interface, some of the light transmits through the interface and some of the light reflects back and is detected by a PIN diode. This process continues until the light intensity fades away. A chemical sensitive material is coated on top of the polyimide to modify the properties of the air/polyimide interface to allow detection of a property of the environment such as the presence of a gas. When the gas to which the material is sensitive appears, the light transmitted from the polyimide to air increases, thus the total signal sensed by the photodetector decreases which indicates chemical detection.

These are apparently the first fully integrated photosensors to use sensitive materials to modify the index of refraction of light traveling in a microchip waveguide core combined with a horizontally mounted LED to inject a reference signal into waveguide core overlying a PIN diode detector.

Additional novel features and advantages incorporated from the co-filed application are a high temperature flip chip die attachment process which can be used with a subsequent polyamide curing process without degrading Si devices, and a TiW diffusion barrier which provides a short circuit free LED contact.

Further, the AuGe layer self-aligned to the LED edge can minimize the reflow and light scattering problem. An additional advantage can be the maximization of light coupling between the LED active layer and the photodetector PIN diode by close vertical alignment.

Other advantages from the integrated chip sensor can include an extremely small device with the potential to integrate with the sensor other components such as a microprocessor to create a smart sensor or a total sensor system.

BRIEF DESCRIPTION OF THE DRAWINGS

The novel features believed characteristic of the invention are set forth in the appended claims. The invention itself, however, as well as other features and advantages thereof, will be best understood by reference to the detailed description which follows, read in conjunction with the accompanying drawings, wherein:

DETAILED DESCRIPTION OF THE PREFERRED EMBODIMENTS

The preferred embodiment of the present invention is best understood by referring to FIGS. 1–5 of the drawings, like numerals are used for like and corresponding parts of the various drawings.

Figure 1:
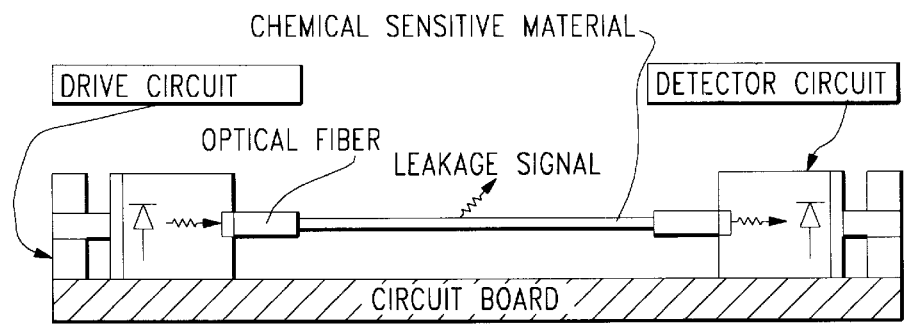
FIG. 1 Represents a chemical sensor of the prior art.

With reference to FIG. 1, there is shown a chemical sensor structure of the prior art. This sensor contains discrete components such as a LED light source, an optical fiber, a waveguide with a chemically sensitive area, a detector diode, and associated drive and detector circuitry, all mounted to a circuit board.

Figure 2:
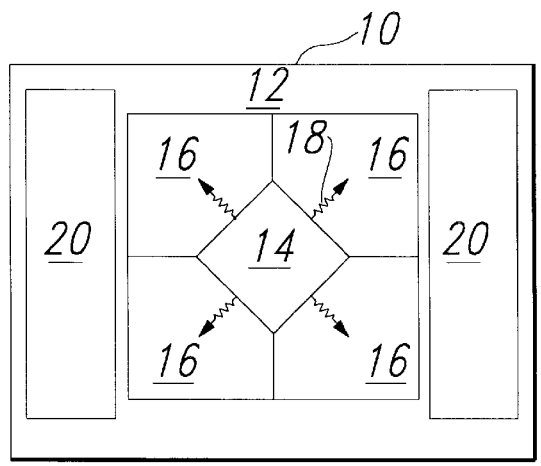
FIG. 2 Shows a plan view of an embodiment of the present invention.

In contrast, FIG. 2 represents a top view of an embodiment of the present invention, an integrated smart sensor. The integrated smart sensor, shown generally at 10, is fabricated on a semiconductor substrate 12. The sensor includes an LED 14 disposed amid four PIN diodes 16 as shown. The LED 14 is preferably an edge emitting double heterojunction GaAs LED which is flip chip mounted to the semiconductor substrate 12. The LED is preferably fabricated to emit light 18 from each face toward each PIN diode as shown by the broken arrows. The edge emitted light signal travels in four directions in a dielectric waveguide on the surface of the PIN diodes. The light signal is detected by PIN diodes 16 as influenced by the chemical or environmental condition to be detected, discussed further hereinbelow. The detected signal may be processed and analyzed by conditioning and processing circuitry 20.

Figure 3:
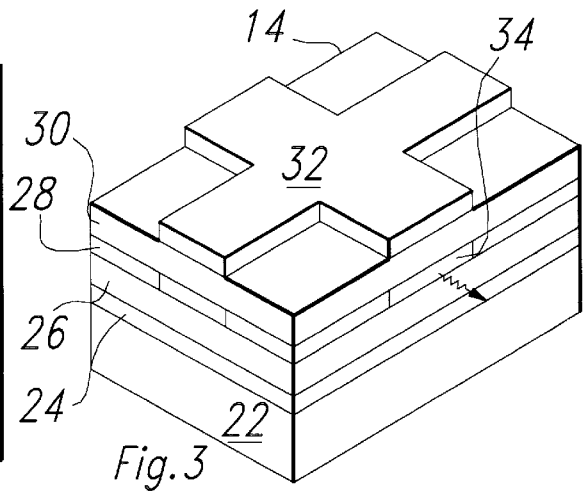
FIG. 3 Shows an isometric view of the LED shown in FIG. 2.

FIG. 3 represents a perspective view of the four directional emitting LED 14 shown in the center of FIG. 2. The LED is preferably a double heterojunction GaAs structure. A GaAs double heterojunction LED epitaxy is preferably grown by Metal Organic Vapor Phase Epitaxy (MOVEP) on a GaAs n+ substrate 22. A GaAs double heterojunction structure can be fabricated by processes known in the art. In a preferred embodiment, layers are grown on a GaAs n-type substrate. First a layer of GaAs n-type 24 is grown, followed by AlGaAs n-type 26 followed by an active layer of GaAs p-type 28. On the active layer a layer of AlGaAs p-type 30 is grown followed by a cap layer of GaAs p-type 32. The double heterojunction AlGaAs/GaAs/AlGaAs structure provides higher emission efficiency for LEDs. An active device area 34 is defined by mesa etching the P+ cap layer, which confines the current flow to underneath the p+ cap region and defines the light emitting area as shown in shaded dark region 34 of FIG. 3.

The shape of the LED 14 shown in FIG. 3 is important for an embodiment of the present invention to allow a single LED to function as a multiple light source for an embodiment of the present invention. The cross shaped active area allows a single current source to activate the LED and emit light at each of the four faces of the active region in the active device areas 34, only two of which are indicated in FIG. 3. The cross shaped active region is preferable over a rectangular one because it reduces the size of the active region which lowers the current necessary to drive the LED and also creates a smaller light source for each of the PIN diodes. A light source which is more of a point source reduces the risk that light emitted from one face of the LED will interact with adjacent PIN diodes, PIN diodes other than that PIN diode directly in front of the LED.

After the LED is fabricated as discussed above, the LED is preferably flip chip mounted to a silicon substrate with PIN diodes as discussed above and shown in FIG. 4. The preferred method for flip-chip mounting is as disclosed in the concurrently filed application Ser. No. 08/808,373 (TI-21382). Briefly, the LED is mounted by forming an anode contact 36 shown in FIG. 4 on the GaAs p-type layer 32 shown in FIG. 3. The contact is formed by evaporating a layer of TiW followed by Au, followed by AuGe. After the anode metal contact is formed, the wafer was then lapped down to 4 mils, and AuGe/Ni/Au evaporated on the backside of the wafer for the n side cathode contact 38.

To prepare the silicon circuit substrate, preferably after the circuit fabrication on the silicon is complete, TiW/Au metal is deposited on the silicon wafer to form alloy pads 40 for the LED to be mounted on. In the illustrated embodiment, a silicon substrate 12, contains PIN diodes fabricated on the surface, where the PIN diodes include P layer 46 and N layer 44. An insulating layer 42 of $SiO_2$ covers the PIN diodes and insulates the diode contacts from the LED anode contact. A single LED die is then mounted directly on top of the silicon PIN diode of the photosensor through the thermal compression of AuGe metal alloy compound at 372 C. After mounting the LED a polyimide waveguide is formed as discussed below.

Figure 4:
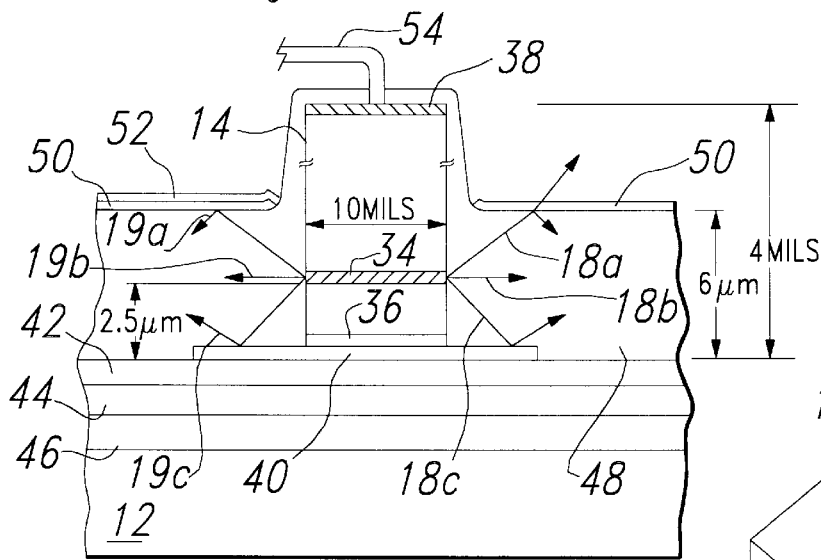
FIG. 4 Illustrates a cross section of an embodiment shown in FIG. 2.

The LED 14 mounted to the silicon semiconductor integrated circuit 12 is shown in FIG. 4. After the LED 14 is mounted as discussed above, the LED cathode contact 38 may be connected to the silicon power supply by a bonding wire 54 as shown. The LED anode contact may be made by extending bond pad layer 40 to a common chip ground.

The silicon substrate may contain one or more PIN diodes. The PIN diodes used in a preferred embodiment are essentially TSL250 series Light-to-Voltage Optical Sensors manufactured by Texas Instruments Incorporated.

Again referring to FIG. 4, the LED 14 emits light 18a,b,c from active area 34 into polyimide waveguide 48 as shown. Light is emitted at all angles between light vectors 18a and 18c, which are acute angles from the light vector 18b. Light emitted essentially parallel to the substrate, such as that shown by light vector 18b, is wasted signal because it does not contribute to measuring the environmental parameter of interest since it does not interact with environmentally sensitive cladding 50. Part of the light, indicated by vector 18a, propagates toward the air/polyimide interface. At the air/polyimide interface, some of the light transmits through the interface and some of the light reflects back and is detected by a PIN diode. This process continues until the light intensity fades away. As used herein, a sensitive cladding is a waveguide cladding made from a material which is sensitive to a characteristic of an environment which is to be monitored. A sensitive cladding material 50, is coated on top of the polyimide 48, so that when the condition to which the material is sensitive appears, the light transmitted from the polyimide to air changes, e.g. increases, thus the total signal sensed by the photodetector e.g. decreases. Thus chemical detection is indicated by the decrease in light detected by the photodetector. In addition, part of the light, indicated by vector 18c, propagates toward the polyimide/photodetector interface. At this interface, some of the light is reflected back into the polyimide, and some is absorbed by the PIN diode. That absorbed by the PIN diode which came directly from the LED contributes to background noise. In a preferred embodiment, the bond pad 40 is extended such that light vector 18c initially hits the bond pad, or some other material which is highly reflective, to reduce background noise by reducing light striking the PIN diode which has not interacted with the sensitive cladding material 50.

Figure 5:
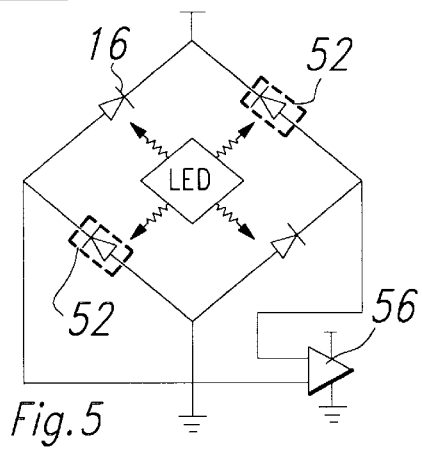
FIG. 5 Shows a schematic of an embodiment using a bridge design for common mode rejection.

While FIG. 4 only shows light emitting from a single face of the LED, the most preferred embodiment of the present invention has light emitting from each of the four sides of the LED as shown from the top in FIG. 2. Light emitting from each face propagates in its respective polyimide waveguide as shown in FIG. 4 to a respective PIN diode. In this most preferred embodiment, the four PIN diodes are connected in a bridge circuit as shown in FIG. 5. Two of the PIN diode waveguides have a protective layer 52 shown in FIGS. 4 and 5. This protective layer prevents the environment from coming in contact with the sensing material for the waveguides for these two PIN diodes and therefore inactivates these two diodes from detecting changes in the environment which is of interest. Substantially all the light 19a,b,c emitted from the LED into a waveguide having a protective layer 52 is sensed by the detector 16 below the protected waveguide. The inactivated PIN diodes serve to enhance the sensitivity of the overall circuit by providing common mode noise rejection by connecting the four PIN diodes in the circuit as shown with a differential amplifier 56 as shown. In a preferred embodiment, the protective layer is aluminum deposited by sputtering or E-beam evaporation. The protective layer can be of any material which will block light from the sensitive cladding and is not be degraded or damaged by the environment.

An advantage of the present invention is the active region 34 is in close proximity to insulating area, in the preferred embodiment about 2.5 µm. In addition, while the overall height of the LED may be as much as 4 mils, the waveguide 48 may be as little as 6 µm. Reduced waveguide dimensions are advantageous because it allows more interaction of the light traveling in the waveguide with the sensitive cladding.

An additional advantage of the present invention is the LED is self aligned. The LED is self aligned compared to prior art structures which required difficult alignment of light source, waveguide and detector. In accordance with an embodiment of the present invention, the LED can be considered self aligned where the waveguide is formed after attachment of the light source to the IC which has a PIN diode for a light source. Also, since the PIN diode has a fairly large surface area, the device can tolerate a good deal of rotational misalignment. In addition, the device according to an embodiment of the present invention may also be highly tolerant placement tolerances.

Experimental data for a preferred embodiment, essentially that shown in FIG. 4, is shown below in Table 1. Data in the first Sensor Output column for $V_1$ is a test made prior to application of the polyimide waveguide layer 48 for a corresponding LED bias current shown in the first column. The $V_2$ is the output voltage after application of the polyimide waveguide layer. Comparison of the data in these two columns demonstrates the waveguide is effective for guiding the light shown by the increase of light incident on the detectors. The next two columns, $V_3$ and $V_4$ demonstrate the LED output when the sensing material is in the presence of alcohol and gasoline respectively. The drop in output indicates the sensing material has changed in index of refraction due to the influence of the alcohol or gasoline in contact with the sensing material.

TABLE 1

Microchip Sensor Test For Alcohol And Gasoline

| LED Bias I(mA) | Sensor Output $V_1$ (no polyimide) | $V_2$ (polyimide) | $V_3$ (Alcohol) | $V_4$ (gasoline) |
|---|---|---|---|---|
| 0.0 | 0.003 | 0.004 | 0.004 | |
| 0.5 | 0.007 | | | |
| 1.0 | 0.045 | 0.085 | 0.069 | 0.085 |
| 1.25 | | 0.187 | 0.151 | 0.160 |
| 1.50 | 0.206 | 0.366 | 0.294 | 0.290 |
| 1.75 | | 0.631 | 0.510 | 0.450 |
| 2.00 | 0.547 | 0.98 | 0.800 | 0.730 |
| 2.25 | | 1.402 | 1.164 | 1.032 |
| 2.50 | 1.049 | 1.888 | 1.604 | 1.379 |
| 2.75 | | 2.44 | 2.130 | 1.765 |
| 3.0 | 1.678 | 3.03 | 2.74 | 2.20 |
| 3.25 | | 3.67 | 3.3 | 2.64 |
| 3.30 | | 3.80 | 3.39 | 2.73 |
| 3.35 | | 3.87 | 3.48 | 2.82 |
| 3.40 | | | 3.52 | 2.91 |
| 3.45 | | | 3.75 | 3.02 |
| 3.50 | 2.45 | | 3.86 | 3.11 |
| 3.75 | | | | 3.62 |
| 3.80 | | | | 3.72 |
| 4.0 | 3.24 | | | 3.87 |
| 4.38 | 3.89 | | | |

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

The Table 2, below, provides an overview of some embodiments and the drawings.

TABLE 2

| Drawing Element | Preferred or Specific Examples | Generic Term | Other Alternate Examples |
|---|---|---|---|
| 10 | Sensor | | |
| 12 | Silicon Substrate | Substrate | GaAs, InP |
| 14 | GaAs LED | LED | InP, InGaAs |
| 16 | PIN Diode | Photosensor or Detector | |
| 18 | Light | Light | |
| 20 | Processing Circuitry | Processing Circuitry | |
| 22 | GaAs n+ Substrate | LED Substrate | |
| 24–32 | GaAs | LED Layers | InP, InGaAs, Group III and V materials |
| 34 | Active Area | | |

TABLE 2-continued

| Drawing Element | Preferred or Specific Examples | Generic Term | Other Alternate Examples |
|---|---|---|---|
| 36 | TiW/Au/AuGe | Anode | TiN/Au/AuGe, TiN/Au/AsSn |
| 38 | AuGe | Cathode | Au, In, Pd |
| 40 | TiW/Au | Bond Pad | |
| 42 | SiO$_2$ | Insulating Layer | Polyimide |
| 44 | Si n-type | Diode Layer | |
| 46 | Si p-type | Diode Layer | |
| 48 | Polyimide | Waveguide | Any organic waveguide material |
| 50 | Paralene | Sensitive Cladding | Other sensitive materials that induce a shift in index of refraction |
| 52 | Aluminum | Protective Layer | W, Ti, Au, or any other opaque material |
| 54 | Bonding Wire | Electrical Contact | |
| 56 | Differential Amplifier | Differential Amplifier | |

What is claimed is:

1. A microchip chemical sensor structure for sensing the presence of a substance in an environment comprising:
   (a) a semiconductor base;
   (b) a source on said base for emitting a light signal;
   (c) at least one light detector integrated into the top surface of said base;
   (d) one or more waveguides between said source and said light detector to couple at least some of the light from said source to said light detectors; and
   (e) a cladding layer comprising a chemical sensitive material disposed on top of at least one of said waveguides such that the index of refraction for a waveguide having said cladding layer of chemical sensitive material will be a function of the concentration of a target chemical in said environment adjacent to said chemical sensitive material.

2. The structure according to claim 1, wherein said source emits light generally parallel and in acute angles to the parallel of said substrate, and at least one of said waveguides is in a plane directly over and parallel to said detector, such that light emitted at angles other than parallel to the detector into said waveguide strike the detector directly or after reflecting from off the cladding layer.

3. The structure according to claim 2, wherein at least one of said waveguides is a layer of polyimide applied over said detector integrated into said base.

4. The structure according to claim 1, wherein at least one of said waveguide has a protective covering between said waveguide core and said cladding layer of chemically sensitive material.

5. The structure according to claim 1, wherein said light source comprises a AuGe thin film for flip-chip die attachment.

6. The structure according to claim 5, wherein said AuGe thin film is self-aligned.

7. The structure according to claim 1, wherein the vertical distance between the LED active layer and the photodetector is less than 4 μm.

8. The structure according to claim 1, further comprising a microprocessor to process the sensor output integrated on said base.

9. The structure according to claim 1, wherein the light detector is a PIN diode.

10. The structure according to claim 1, further comprising;
    (f) at least four light detectors arranged to detect light from one or more LEDs;
    (g) at least two of said waveguide cores which guide light to said light detectors are coated with said chemically sensitive material; and
    (h) at least two of said waveguide cores which guide light to said light detectors are not coated with said chemically sensitive material and are thereby protected from the change in index of refraction due to the presence of the property to be sensed in the environment;
    wherein said light detectors are arranged in a bridge circuit with a differential output, in such a way to provide common mode rejection of noise and error due to processing anomalies and/or imbalance of exposure of the chemically sensitive material.

11. An integrated microchip chemical sensor structure for sensing the presence of a substance in an environment comprising:
    (a) a semiconductor substrate;
    (b) an LED structure disposed on the lateral surface of said semiconductor substrate for emitting a light signal;
    (c) one or more light detectors disposed in said semiconductor substrate;
    (d) one or more waveguides between said LED structure and said light detectors to couple at least some of the light from said LED structure to said light detectors wherein at least one of said waveguides is a layer of polyimide applied over said detector; and
    (e) a cladding layer comprising a chemical sensitive material disposed on each of said waveguides, such that the index of refraction for a waveguide having said cladding layer of chemical sensitive material will be a function of the concentration of a target chemical in said environment adjacent to said chemical sensitive material.

12. The structure according to claim 11, wherein said source emits light generally parallel and in acute angles to the parallel of said substrate, and at least one of said waveguides is in a plane directly over and parallel to said detector, such that light emitted at angles other than parallel to the detector into said waveguide may strike the detector directly or after reflecting off the cladding layer.

13. The structure according to claim 12, wherein said detector is a PIN diode integrated into the surface of said substrate.

14. The structure according to claim 11, wherein at least one of said waveguide cores has a protective covering between said waveguide core and said cladding layer of chemically sensitive material.

15. The structure according to claim 11, wherein said LED further comprises a AuGe thin film for flip-chip die attachment.

16. The structure according to claim 11, wherein said AuGe thin film is self-aligned.

17. The structure according to claim 11, wherein the vertical distance between the LED active layer and the photodetector is less than 4 μm.

18. The structure according to claim 11, further comprising a microprocessor to process the sensor output integrated on said substrate.

19. The structure according to claim 11, further comprising;
    (f) at least four light detectors arranged to detect light from one or more LEDs;
    (g) at least two of said waveguide cores which guide light to said light detectors are coated with said chemically sensitive material; and (h) at least two of said waveguide cores which guide light to said light detectors are not coated with said chemically sensitive material and are thereby protected from the change in index of refraction due to the presence of the property to be sensed in the environment;

wherein said light detectors are arranged in a bridge circuit with a differential output, in such a way to provide common mode rejection of noise and error due to processing anomalies and/or imbalance of exposure of the chemically sensitive material.

20. An integrated microchip chemical sensor structure for sensing the presence of a substance in an environment comprising:

(a) a semiconductor substrate;

(b) an LED structure disposed on the lateral surface of said semiconductor substrate for emitting a light signal;

(c) one or more light detectors integrated into the surface of said semiconductor substrate;

(d) one or more waveguides between said LED structure and said light detectors to couple at least some of the light from said LED structure to said light detectors wherein at least one of said waveguides is a layer of polyimide applied over said detector;

(e) a cladding layer comprising a chemical sensitive material disposed on each of said waveguides, such that the index of refraction for a waveguide having said cladding layer of chemical sensitive material will be a function of the concentration of a target chemical in said environment adjacent to said chemical sensitive material; and (f) a microprocessor to process the sensor output integrated on said substrate.

21. The structure according to claim 20, wherein said source emits light generally parallel and in acute angles to the parallel of said substrate, and at least one of said waveguides is in a plane and parallel to said detector, such that light emitted at angles other than parallel to the detector into said waveguide may strike the detector directly or after reflecting off the cladding layer.

22. The structure according to claim 20, wherein at least one of said waveguide cores has a protective covering between said waveguide core and said cladding layer of chemically sensitive material.

23. The structure according to claim 20, wherein said LED further comprises a self-aligned AuGe thin film for flip-chip die attachment.

24. The structure according to claim 20, further comprising;

(f) at least four light detectors arranged to detect light from one or more LEDs;

(g) at least two of said waveguide cores which guide light to said light detectors are coated with said chemically sensitive material; and (h) at least two of said waveguide cores which guide light to said light detectors are not coated with said chemically sensitive material and are thereby protected from the change in index of refraction due to the presence of the property to be sensed in the environment;

wherein said light detectors are arranged in a bridge circuit with a differential output, in such a way to provide common mode rejection of noise and error due to processing anomalies and/or imbalance of exposure of the chemically sensitive material.

* * * * *